United States Patent
Freed

(10) Patent No.: US 8,500,088 B2
(45) Date of Patent: Aug. 6, 2013

(54) CONTAINER AND PHARMACEUTICAL PRODUCT

(75) Inventor: Simon Freed, Hillsborough, NJ (US)

(73) Assignees: Baxter International Inc., Deerfield, IL (US); Baxter Healthcare SA, Glattpark (Opfikon) (CH)

(*) Notice: Subject to any disclaimer, the term of this patent is extended or adjusted under 35 U.S.C. 154(b) by 345 days.

(21) Appl. No.: 12/783,337

(22) Filed: May 19, 2010

(65) Prior Publication Data

US 2010/0294277 A1 Nov. 25, 2010

Related U.S. Application Data

(60) Provisional application No. 61/179,921, filed on May 20, 2009.

(51) Int. Cl.
*F16L 37/28* (2006.01)
(52) U.S. Cl.
USPC .............. 251/149.7; 251/149.3; 128/203.16
(58) Field of Classification Search
USPC ............. 251/149.6, 149.7, 149.3; 128/203.16
See application file for complete search history.

(56) References Cited

U.S. PATENT DOCUMENTS

| | | | |
|---|---|---|---|
| 3,416,577 A | 12/1968 | Franz | |
| 4,625,779 A | 12/1986 | Ryschka et al. | |
| 4,693,853 A | 9/1987 | Falb et al. | |
| 4,825,860 A | 5/1989 | Falb et al. | |
| 4,862,918 A | 9/1989 | Schroeder | |
| 4,867,212 A | 9/1989 | Mohr et al. | |
| 4,879,997 A | 11/1989 | Bickford | |
| 4,883,049 A | 11/1989 | McDonald | |
| 4,893,659 A | 1/1990 | Loliger | |

(Continued)

FOREIGN PATENT DOCUMENTS

| | | |
|---|---|---|
| DE | 102004043652 | 10/2005 |
| EP | 0678042 | 10/1995 |

(Continued)

OTHER PUBLICATIONS

International Search Report and Written Opinion for corresponding International Application No. PCT/US2010/035423, dated Jul. 28, 2010 (9 pp.).

(Continued)

*Primary Examiner* — John K Fristoe, Jr.
*Assistant Examiner* — Ian Paquette
(74) *Attorney, Agent, or Firm* — Marshall, Gerstein & Borun LLP

(57) ABSTRACT

An anesthetic container includes a receptacle for holding the anesthetic and having a wall defining an interior space and a passage in fluid communication with the interior space. The container also includes a valve assembly that is attachable or is attached to the receptacle to control flow of anesthetic through the passage in the receptacle to a vaporizer. The valve assembly has a closed configuration when the flow of anesthetic from the receptacle is limited and an open configuration when the flow of anesthetic is enabled. The valve assembly is constructed so that at least the surface of any component of the assembly that will come into contact with the anesthetic on its storage or passage from the receptacle to the vaporizer is made of a metal or low-density polyethylene, and provides a fluid-tight seal to prevent the escape of the anesthetic without the use of a gasket in the closed configuration.

14 Claims, 4 Drawing Sheets

U.S. PATENT DOCUMENTS

| | | | |
|---|---|---|---|
| 4,932,398 A | | 6/1990 | Lancaster et al. |
| 5,018,644 A | * | 5/1991 | Hackmann et al. ............. 221/65 |
| 5,048,874 A | | 9/1991 | Ohlsson |
| 5,144,984 A | | 9/1992 | Westerberg et al. |
| 5,144,991 A | | 9/1992 | Wallroth et al. |
| 5,170,823 A | | 12/1992 | Gregory et al. |
| 5,287,898 A | | 2/1994 | Falb et al. |
| 5,381,836 A | | 1/1995 | Braatz et al. |
| 5,419,316 A | | 5/1995 | Bernstein |
| 5,427,145 A | | 6/1995 | Grabenkort |
| 5,474,112 A | | 12/1995 | Carola |
| 5,478,506 A | | 12/1995 | Lavimodiere |
| 5,505,236 A | | 4/1996 | Grabenkort et al. |
| 5,509,433 A | * | 4/1996 | Paradis ............................. 137/1 |
| 5,536,047 A | | 7/1996 | Detable et al. |
| 5,585,045 A | | 12/1996 | Heinonen et al. |
| 5,617,906 A | | 4/1997 | Braatz et al. |
| 5,653,475 A | | 8/1997 | Scheyhing et al. |
| 5,682,874 A | | 11/1997 | Grabenkort et al. |
| 5,687,777 A | | 11/1997 | Dobson et al. |
| 5,740,835 A | | 4/1998 | Murphy |
| 5,758,640 A | | 6/1998 | Kamppari et al. |
| 5,799,711 A | | 9/1998 | Heinonen et al. |
| 5,810,001 A | | 9/1998 | Genga et al. |
| 5,839,487 A | | 11/1998 | Moll et al. |
| 5,860,502 A | | 1/1999 | Grosspietsch et al. |
| 5,911,250 A | | 6/1999 | Turker et al. |
| 5,915,427 A | | 6/1999 | Grabenkort |
| 5,983,964 A | | 11/1999 | Zielinksi et al. |
| 6,125,893 A | | 10/2000 | Braatz et al. |
| 6,138,672 A | | 10/2000 | Kankkunen |
| 6,149,206 A | | 11/2000 | DiRocco |
| 6,231,084 B1 | | 5/2001 | Hester et al. |
| 6,371,528 B1 | | 4/2002 | Kimura |
| 6,394,087 B1 | | 5/2002 | Kankkunen et al. |
| 6,585,016 B1 | | 7/2003 | Falligant et al. |
| 6,637,725 B2 | | 10/2003 | Davis et al. |
| 6,672,306 B2 | | 1/2004 | Loser et al. |
| 6,676,172 B2 | | 1/2004 | Alksnis |
| 6,745,765 B2 | | 6/2004 | Kullik et al. |
| 6,745,800 B1 | | 6/2004 | Sansom |
| 6,789,698 B2 | | 9/2004 | Gloor et al. |
| 6,817,390 B2 | | 11/2004 | Falligant et al. |
| 6,929,041 B2 | | 8/2005 | Falligant et al. |
| 6,948,642 B2 | | 9/2005 | Awad |
| 7,168,467 B2 | | 1/2007 | Turker et al. |
| 7,290,571 B2 | | 11/2007 | Bunke et al. |
| 7,389,801 B2 | | 6/2008 | Turker et al. |
| 7,472,700 B2 | | 1/2009 | Gershteyn |
| 7,546,856 B2 | | 6/2009 | Chotenovsky |
| 2003/0075241 A1 | | 4/2003 | Videbrink |
| 2004/0206417 A1 | | 10/2004 | Falligant et al. |
| 2005/0145296 A1 | | 7/2005 | Burr |
| 2006/0048842 A1 | | 3/2006 | Bunke et al. |
| 2006/0130930 A1 | * | 6/2006 | Turker et al. .................. 141/351 |
| 2007/0199616 A1 | * | 8/2007 | Chotenovsky ............... 141/351 |
| 2007/0204931 A1 | | 9/2007 | Freed et al. |
| 2007/0204932 A1 | | 9/2007 | Freed et al. |
| 2008/0308179 A1 | | 12/2008 | Danielsen |
| 2008/0319422 A1 | | 12/2008 | Cardenas |
| 2009/0255532 A1 | | 10/2009 | Grunstad et al. |
| 2009/0260627 A1 | | 10/2009 | Cuzydlo et al. |
| 2010/0018528 A1 | | 1/2010 | Cuzydlo |
| 2010/0018607 A1 | | 1/2010 | Cuzydlo |

FOREIGN PATENT DOCUMENTS

| | | |
|---|---|---|
| WO | WO 95/26772 | 10/1995 |
| WO | WO 96/06301 | 2/1996 |
| WO | WO 2008/048947 | 4/2008 |
| WO | WO 2010/002658 | 1/2010 |

OTHER PUBLICATIONS

Schulte et al., Discolored Desflurane in the Vaporizer, *Anesthesia & Analgesia*, 110:644-45 (2010) (2 pp.).

* cited by examiner

CONTAINER AND PHARMACEUTICAL PRODUCT

This patent claims the benefit of U.S. Application No. 61/179,921, filed May 20, 2009, which is hereby incorporated by reference in its entirety in the present application.

BACKGROUND

This patent is directed to an anesthetic container and a pharmaceutical product, and, in particular, to an anesthetic container and a pharmaceutical product to be used with a halogenated anesthetic.

Liquid anesthetic is conventionally shipped from the manufacturer to the user (medical professional, hospital, etc.) in a container. While the design of the container may vary, it is often the case that the container will include an adapter with a valve assembly disposed in the neck of the container. The valve assembly controls the flow of liquid anesthetic from the container into a vaporizer, where the liquid anesthetic vaporizes typically in the presence of a carrier gas. The valve assembly may also control the return flow of vapor from the vaporizer into the container as the liquid is displaced from the container.

U.S. Patent Application No. 20060048842 illustrates one example of such a valve assembly (or valve, for short). A valve member and associated cylindrical partition move within a conduit or neck to control the exchange of liquid anesthetic and anesthetic vapor with a vaporizer. The illustrated valve or valve assembly is held in place through the cooperation of a rim of a cage, a rim disposed about the container neck, and a crimped ferrule. To seal the connection between the rim of the cage and the rim of the neck, a deformable gasket is disposed between the opposing rims. While not illustrated, a deformable gasket is disposed on the valve member, to seal the valve member to the neck when the valve member is in the closed position.

While different configurations of valve assembly have been tried over the years, it has remained conventional practice to place a gasket between the valve assembly and the container, and between the valve member and the neck. Loss of seal between the valve assembly and the container, or between the valve member and the neck, could have a multiple negative consequences. For example, leakage of anesthetic from the container into the environment is generally undesirable. Additionally, leakage of anesthetic represents a loss of value to the customer and to the supplier, from whom the customer is likely to seek compensation for the lost product.

However, the presence of the sealing gaskets in the assembly is not without its own set of consequences. The additional part count represented by the inclusion of these gaskets may add to the manufacturing costs and complexity. Further, each part within the assembly must be verified for safety, relative to its use in a medical device or system. Additionally, each part within the assembly must be verified for quality, relative to its intended use.

As set forth in more detail below, the present disclosure sets forth a container with an improved valve assembly embodying advantageous alternatives to the valve assemblies of prior art devices.

SUMMARY

In one aspect, an anesthetic container includes a receptacle for holding the anesthetic and having a wall defining an interior space and a passage in fluid communication with the interior space. The container also includes a valve assembly that is attachable or is attached to the receptacle to control flow of anesthetic through the passage in the receptacle to a vaporizer. The valve assembly has a closed configuration when the flow of anesthetic from the receptacle is limited and an open configuration when the flow of anesthetic is enabled. The valve assembly is constructed so that at least the surface of any component of the assembly that will come into contact with the anesthetic on its storage or passage from the receptacle to the vaporizer is made of a metal or low-density polyethylene, and provides a fluid-tight seal to prevent the escape of the anesthetic without the use of a gasket in the closed configuration.

In another aspect, an anesthetic container includes a receptacle having a wall defining an interior space and a passage in fluid communication with the interior space; and a valve assembly to control flow of anesthetic through the passage in the receptacle, the valve assembly attached to the receptacle. The valve assembly includes a conduit (which may be formed using low-density polyethylene) and having a wall defining a conduit passage with a first end and a second end and also a valve member (that may also be formed using low-density polyethylene) and having a first end that is disposed in the second end of the conduit passage when the valve member is in the closed position, and that is spaced from the second end of the conduit passage when the valve member is in the open position. In a further aspect, the second end of the conduit and valve member are formed to create a gasketless, fluid seal therebetween with the valve member in the closed position.

Additional aspects of the disclosure are defined by the claims of this patent.

BRIEF DESCRIPTION OF THE DRAWINGS

It is believed that the disclosure will be more fully understood from the following description taken in conjunction with the accompanying drawings. Some of the figures may have been simplified by the omission of selected elements for the purpose of more clearly showing other elements. Such omissions of elements in some figures are not necessarily indicative of the presence or absence of particular elements in any of the exemplary embodiments, except as may be explicitly delineated in the corresponding written description. None of the drawings is necessarily to scale.

DETAILED DESCRIPTION OF VARIOUS EMBODIMENTS

Although the following text sets forth a detailed description of different embodiments of the invention, it should be understood that the legal scope of the invention is defined by the words of the claims set forth at the end of this patent. The detailed description is to be construed as exemplary only and does not describe every possible embodiment of the invention since describing every possible embodiment would be impractical, if not impossible. Numerous alternative embodiments could be implemented, using either current technology or technology developed after the filing date of this patent, which would still fall within the scope of the claims defining the invention.

It should also be understood that, unless a term is expressly defined in this patent using the sentence "As used herein, the term '_____' is hereby defined to mean . . . " or a similar sentence, there is no intent to limit the meaning of that term, either expressly or by implication, beyond its plain or ordinary meaning, and such term should not be interpreted to be limited in scope based on any statement made in any section of this patent (other than the language of the claims). To the extent that any term recited in the claims at the end of this patent is referred to in this patent in a manner consistent with a single meaning, that is done for sake of clarity only so as to not confuse the reader, and it is not intended that such claim term be limited, by implication or otherwise, to that single meaning. Finally, unless a claim element is defined by reciting the word "means" and a function without the recital of any structure, it is not intended that the scope of any claim element be interpreted based on the application of 35 U.S.C. §112, sixth paragraph.

Figure 1:
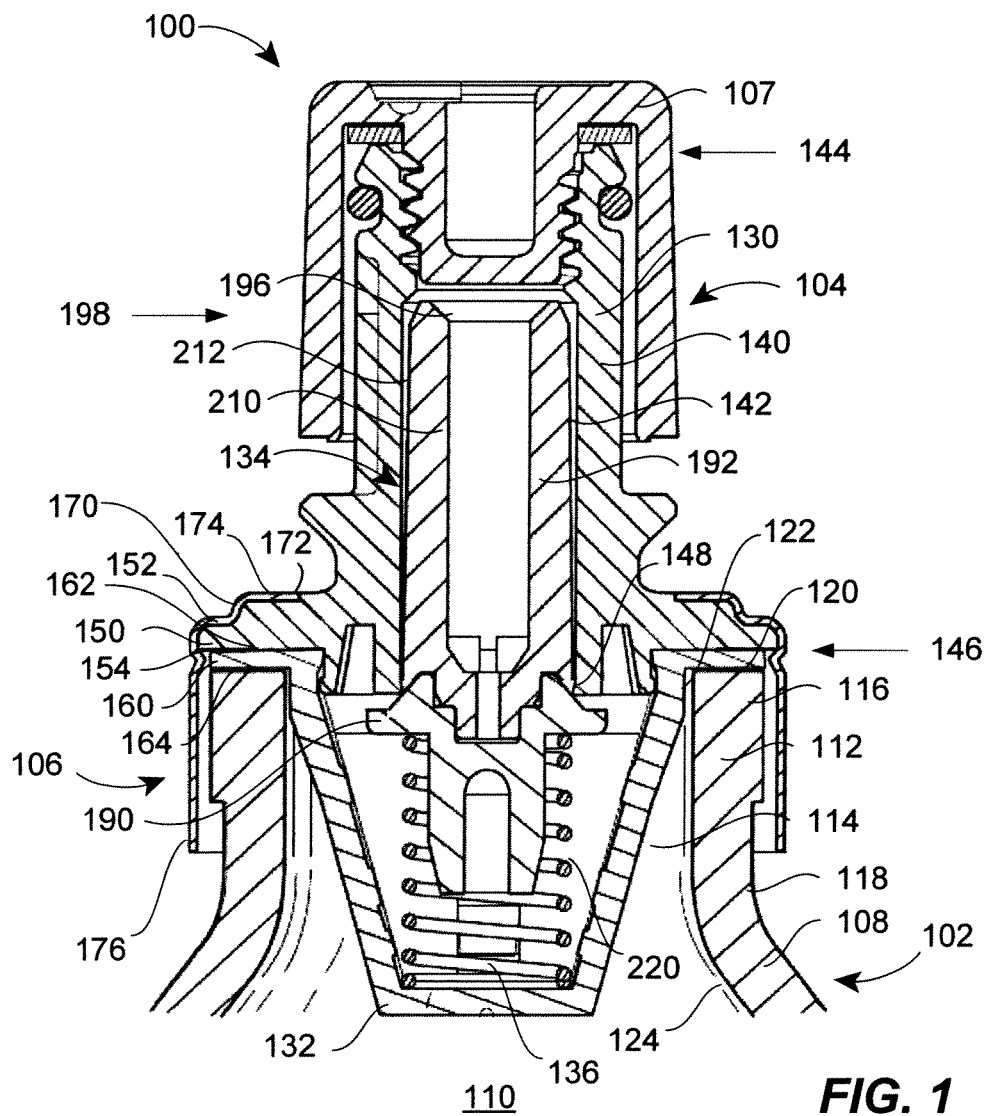
FIG. 1 is a fragmentary, cross-sectional view of a container according to the present disclosure, with a valve assembly in a closed position.

FIG. 1 illustrates an embodiment of an anesthetic container 100. The container 100 may be used with halogenated inhalation anesthetics such as sevoflurane (fluoromethyl 2,2,2-trifluoro-1-[trifluoromethyl]ethyl ether), desflurane (1,2,2,2-tetrafluoroethyl difluoromethyl ether), isoflurane (1-chloro-2,2,2-trifluoroethyl difluoromethyl ether), enflurane (2-chloro-1,1,2-trifluoroethyl-difluoromethyl ether), methoxyflurane (2,2-dichloro-1,1-difluoroethyl methyl ether) and halothane (2-bromo-2-chloro-1,1,1-trifluoroethane), for example, which may be disposed in the container to define a pharmaceutical product. According to certain embodiments, the anesthetic may be selected from a group consisting of sevoflurane, desflurane, isoflurane, enflurane, methoxyflurane and halothane. All of these halogenated anesthetics may be liquids under ambient conditions.

The container 100 includes a receptacle 102 for holding the anesthetic, a valve assembly 104, and a ferrule (or cover) 106. The container 100 may also include a cap 107 that is fitted over the end of the valve assembly 104, as illustrated. The cap 107 may provide a barrier to anesthetic loss as well as limiting access to and contamination of the valve assembly 104.

The receptacle 102 (which may in the form of a bottle as illustrated) has a wall 108 that defines an interior space 110 and a neck 112 with a passage 114 in fluid communication with the interior space 110. The anesthetic may be disposed in the interior space 110. As illustrated in FIG. 1, the embodiment of the receptacle 102 has a neck 112 with a smaller cross-section than the widest part of the receptacle 102; this need not be the case according to all embodiments of the present disclosure. In addition, the receptacle 102 has a flange 116, preferably positioned at the neck 112 of the receptacle 102. As illustrated in FIG. 1, the flange 116 may depend from an exterior surface 118 of the wall 108 to define a rim 120 about an opening 122 in communication with the passage 114 through the neck 112.

According to an embodiment of the present disclosure, the receptacle 102 is made of glass. According to other embodiments, the receptacle 102 may be made of metal, for example, steel, aluminum or an aluminum alloy; according to still other embodiments, the receptacle 102 may be made of a polymer, such as polyethylene terephthalate (PET). Furthermore, according certain embodiments, a polymer or other material may be applied as a thin layer to define the exterior surface 118 of the wall 108. Additionally, according to further embodiments, a polymer or other material may be applied as a thin layer to define an interior surface 124 of the wall 108.

The valve assembly 104 is attachable or is attached to the receptacle 102 to control flow of fluids (e.g., anesthetic) through the passage 114 out of (and in to) the receptacle 102 to (and from) a vaporizer. The valve assembly 104, as illustrated, includes a conduit 130, a cage (or basket) 132, a valve member (or core) 134, and a resilient or biasing member 136. Other elements may be included as well, but as explained in greater detail below, the valve assembly 104 is designed to be gasketless in regard to the interface between the valve assembly 104 and the receptacle 102, and the interface within the valve assembly 104 between the valve member 134 and the conduit 130.

Beginning then with the conduit 130, the conduit 130 has a cylindrical wall 140 that defines a passage 142 with a first end 144 and a second end 146. The cylindrical wall 140 may form a rim 148 (see FIG. 2) disposed about the second end 146 of the passage 142. The conduit 130 also includes a conduit flange 150 that depends outwardly from the wall 140. The conduit flange 150 is disposed proximate to the second end 146 of the passage 142, as illustrated. The conduit flange 150 has opposing first and second surfaces 152, 154.

The cage 132 has a cage flange 160 that is disposed between the conduit flange 150 and the neck 112 of the receptacle 102. In particular, the cage flange 160 has opposing first and second surfaces 162, 164, and the first surface 162 of the cage flange 160 abuts the second surface 154 of the conduit flange 150, while the second surface 164 of cage flange 160 abuts the exterior surface 118 of the receptacle 102 in the region of the neck 112 (more particularly, the rim 120). The cage flange 160 is in direct contact with the neck 112, without any intervening structures therebetween. That is, no gasket is disposed between the conduit flange 150 and/or cage flange 160 and the neck 112 of the receptacle 102 (more particularly, the rim 120 of the receptacle 102).

Alternatively, the conduit flange 150 may abut the exterior surface 118 of the receptacle 102 directly, without even the cage flange 160 intervening between the conduit flange 150 and the exterior surface 118. According to such an embodiment, the cage 132 may be attached to the conduit 130 directly, for example by snapping on to the conduit 130 or by some other attachment mechanism. The cage 132 may be attached to the conduit 130 permanently as a consequence, or may be detachable from the conduit 130.

Although no gasket is disposed between the cage flange 160 and the neck 112 of the receptacle 102, a fluid-tight seal is formed. In particular, a layer of resilient polymer defines the exterior surface 118 of the receptacle 102, at least in the region of the neck 112 of the receptacle 102. For example, a layer of low-density polyethylene may be disposed on a layer of aluminum or aluminum alloy in the region of the neck 112 of the receptacle 102. According to certain embodiments, the low-density polyethylene may be applied using powder coating techniques, in particular where the wall 108 of the receptacle 102 is includes a layer of aluminum or an aluminum alloy. Other methods of including or applying the low-density polyethylene may also be used.

It should be noted that the entirety of the wall 108 of the receptacle 102 need not include the layer of low-density polyethylene. For example, it may be that other regions of the wall 108 of the receptacle 102 include other polymers, as discussed above. According to an exemplary embodiment, the receptacle 102 may include a wall 108 with a layer of a lacquer or an enamel disposed on a layer of aluminum or aluminum alloy, the layer of lacquer or enamel defining, at least in part, the interior surface 124 of the wall 108 of the receptacle 102. According to certain embodiments, the lacquer or enamel may include an epoxyphenolic resin.

As illustrated, the ferrule 106 is disposed over at least a portion of the conduit flange 150 and the cage flange 160 and about at least a portion of the neck 112 to attach the valve assembly 104 to the receptacle 102. The ferrule 106 has a cylindrical shape, with a first end 170 having an opening 172 with a rim 174 disposed about the opening 172 and defining the opening 172. The conduit 130 depends through the opening 172 in the first end 170 of the ferrule 106. The second end 176 of the ferrule 106 may be crimped about the flange 116 of the receptacle 102 to attach the valve assembly 104 to the receptacle 102.

While the illustrated embodiment of the present disclosure has been illustrated with the valve assembly 104 attached to the receptacle 102 with a ferrule 106, it will be recognized that the container 100 need not be only defined as such. For example, the valve assembly 104 may be in the form of an adapter that is mated with the receptacle 102 only just prior to use, the passage 114 being closed instead through the use of a cap that may be threaded on to the receptacle 102 or held in place by a "snap-off" fit. According to such an embodiment, the cap is removed from the receptacle 102 prior to use, and the valve assembly 104 inserted into the passage 114 to attach the valve assembly 104 to the container. As such, the embodiment of the container 100 thus defined does not require the ferrule 106 illustrated in FIG. 1.

Figure 3:
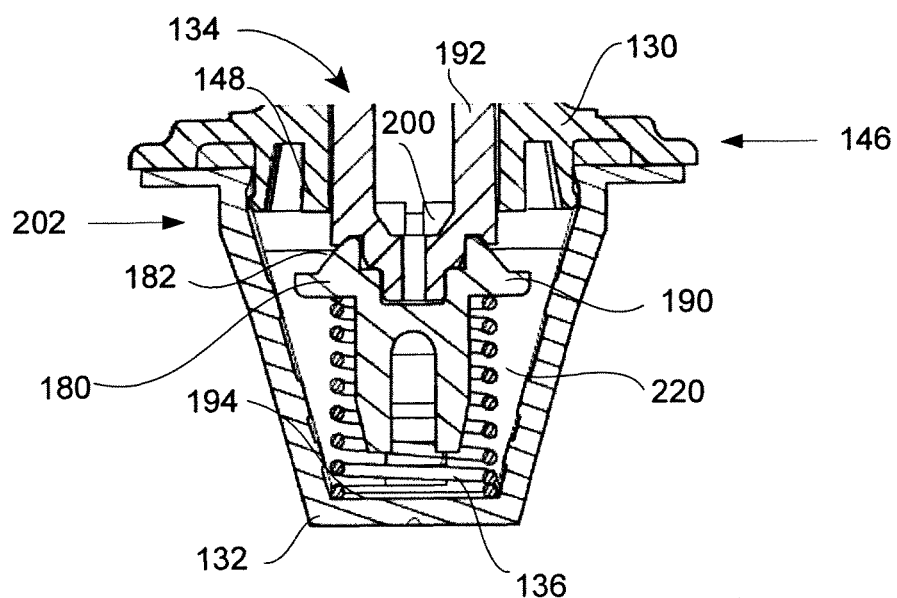
FIG. 3 is a partial cross-sectional view of the valve assembly of FIG. 1, with the receptacle and the ferrule removed and the valve assembly in an open position.

Turning next to FIG. 3, it will be recognized that the valve member 134 is disposed between the conduit 130 and the cage 132. The valve member 134 has a first end 180 that is disposed in the second end 146 of the passage 142 when the valve member 134 is in the closed position (as seen in FIG. 1). This may coincide with a closed configuration of the valve assembly 104. The valve member 134 is spaced from the second end 146 of the passage 142 when the valve member 134 is in the open position (FIG. 3). This may coincide with an open configuration of the valve assembly 104.

The valve member 134 may have conical or tapered surface 182 formed at the first end 180. While the surface 182 has a constant slope as illustrated, it will be recognized that the surface 182 may actually have a first region with a first slope and a second region with a second slope, for example. According to the illustrated embodiment, the rim 148 of the conduit 130 may directly contact the conical surface 182 with the valve member 134 in the closed position. An edge of the rim 148 is configured to concentrate the contact forces between the conduit 130 and surface 182 to define a fluid-tight seal (see FIG. 2). In an embodiment, the rim 148 may be formed to define a generally right angle edge. In a further embodiment the rim 148 may be slightly outwardly flared. In a further embodiment, the rim 148 may be formed with a narrow, downwardly and inwardly flaring frusto-conical surface that flares inward to form an upper and a lower edge. The surface would flare at an angle that is greater than the angle formed by the conical surface 182. Having different angles for the opposing conical surface causes the upper edge of the rim to contact the surface 182 with a concentrated force. Accordingly, the second end 146 of the conduit passage 142 and the valve member 134 forms a gasketless, fluid-tight seal formed therebetween with the valve member 134 in the closed position (FIG. 1) according to this embodiment; it will be recognized that other configurations that define gasketless, fluid seals may also be used.

Elimination of the gasket provides an advantage by eliminating a material that comes into contact with the fluid, thereby eliminating a potential source of extractables or leachables that may impact the shelf life or other characteristic of the fluid. As observed by Schulte and Ellis, in Anesthesia and Analgesia, vol. 2, no. 2, pp. 644-645 (February 2010), a yellow discoloration may result from use of conventional anesthetic containers, which containers include the use of gaskets. While they report that no patient harm is likely to result, the limitation or elimination of the compounds reported by Schulte and Ellis is believed to be possible through the elimination of gaskets in the anesthetic container.

This fluid tight-seal is formed in the preceding embodiment by virtue of the interface between the rim 148 and the conical surface 182, and despite the fact that the conduit 130 and the first end 180 of the valve member 134 are molded from low-density polyethylene. Conventional thought would suggest that to obtain a fluid-tight seal, at least one of the surfaces should be softer than the other surface. This thought is particularly reinforced when the fluid in the receptacle 102 is desflurane that has a low boiling point. However, in this regard, it has been found that the nature of the cooperation between the edge of the rim 148 and the conical surface 182 provides an adequate seal relative to liquid or vapor leakage such that both the conduit 130 and the valve member 134 may be molded using low-density polyethylene. Depending on the polyethylene selected, the material may require the use of inserts, however, to provide sufficient stiffness to the molded structures.

It is believed that the use of such a gasketless arrangement does not result in increased losses of anesthetic. In particular, tests were performed using thirty-two (32) containers fabricated in accordance with the embodiment of FIGS. 1-3 and thirty-two (32) conventional containers, such as were discussed by Schulte and Ellis. Each of the containers was activated by inserting and removing the container from a vaporizer fill port nine (9) times. The bottles were then stored upright in a temperature and humidity controlled chamber at 40° C. for one hour without valve caps. After removal from the chamber and allowing for equilibration to room conditions, the weight change of each individual bottle was measured. The weight loss for the containers fabricated in accordance with the embodiment of FIGS. 1-3 was slightly better than the conventional containers, with a smaller standard deviation as well. The test results are summarized as follows:

| Conventional Container Loss (g) | | Containers (FIGS. 1-3) Loss (g) | |
|---|---|---|---|
| Average | 0.048 | Average | 0.045 |
| Max. | 0.067 | Max. | 0.055 |
| Min. | 0.032 | Min. | 0.031 |
| Std. Dev. | 0.011 | Std. Dev. | 0.005 |

The use of low-density polyethylene in the valve assembly 104 may have additional advantages as well. For instance, the conduit 130 and the valve member 134 are conventionally molded using nylon. Low-density polyethylene is less expensive that using nylon to mold the elements of the valve assembly 104. Also, it is believed that nylon may have a tendency to absorb moisture over time, causing swelling of the parts and leading to operational issues. Furthermore, it has been found that replacing nylon with low-density polyethylene may lead to a reduction in instrument errors that may occur when a container including a conventional valve assembly is used.

In this last regard, it will be recognized that conventional vaporizers rely upon a capacitance sensor (using the anesthetic as the dielectric) to determine the amount of anesthetic present. Unfortunately, using a conventionally constructed container, these capacitance sensors often read as if there was more anesthetic in the container than would be determined using other measuring technologies. It has been found that the replacement of nylon with low-density polyethylene may reduce the errors between the sensed and actual values.

Still with reference to FIG. 3, it will be recognized that the valve member 134 includes a plate (or core seat) 190 and a tube (or core extension) 192, as illustrated. It will be recognized that other valve members may be designed wherein the plate 190 and tube 192 are formed as a single unit (i.e., integrally with each other). Thus, the illustrated embodiment is not intended to be limiting in this regard.

The plate 190 defines the first end 180 of the valve member 134, and thus occludes the second end 146 of the passage 142 through the conduit 130 with the valve member 134 in the closed position. The valve member 134 is biased towards a closed position, illustrated in FIG. 3, through the action of the resilient member 136, which may be a spring, as illustrated. The resilient member 136 is disposed between the valve member 134 and the cage 132, and specifically the plate 190 of the valve member 134 and a surface 194 of the cage 132.

The tube 192 is an exemplary structure or partition that may be included in the valve member 134 to guide the flow of more than one fluid at a time. In particular, the tube 192 has an opening 196 at a first end 198 (see FIG. 1) and at least one opening 200 at a second end 202 (see FIG. 3); as illustrated, a plurality of openings 200 are provided in the second end 202. While the tube 192 is illustrated as coaxial with the conduit 130, this need not be the case according to all embodiments of the present disclosure.

The tube 192 depends from the plate 190. The tube 192 is configured with an interior surface which is preferably generally cylindrical to define a passage 210 through the tube. A series of ribs extend along a portion of the length and outwardly from an outer surface 212 of the tube 192 to close proximity to the cylindrical wall 140 to define annular gaps or passageways between the tube 192 and the conduit 130. In an embodiment, there are four ribs spaced equally around the outer circumference of the tube 192 that define four annular passageways.

In operation, when the valve member 134 is biased away from the closed position (through interaction between the tube 192 and a structure of the vaporizer, for example), liquid anesthetic is permitted to flow through openings 220 in the cage 132, the second end 146 of the conduit 130, and the passageways defined between the tube 192 and the conduit 130 into an associated vaporizer. At the same time, the first end 198 of the tube 192 is in fluid communication with a portion of the vaporizer through which vapor and possibly some fluid returns to the receptacle 102. This vapor and possible fluid passes through the opening 196 in the first end 198 of the tube 192, through the passage 210 defined through the tube 192, out of the at least one of the openings 200 in the second end 202 of the tube 192, and into the receptacle 102.

Figure 4:
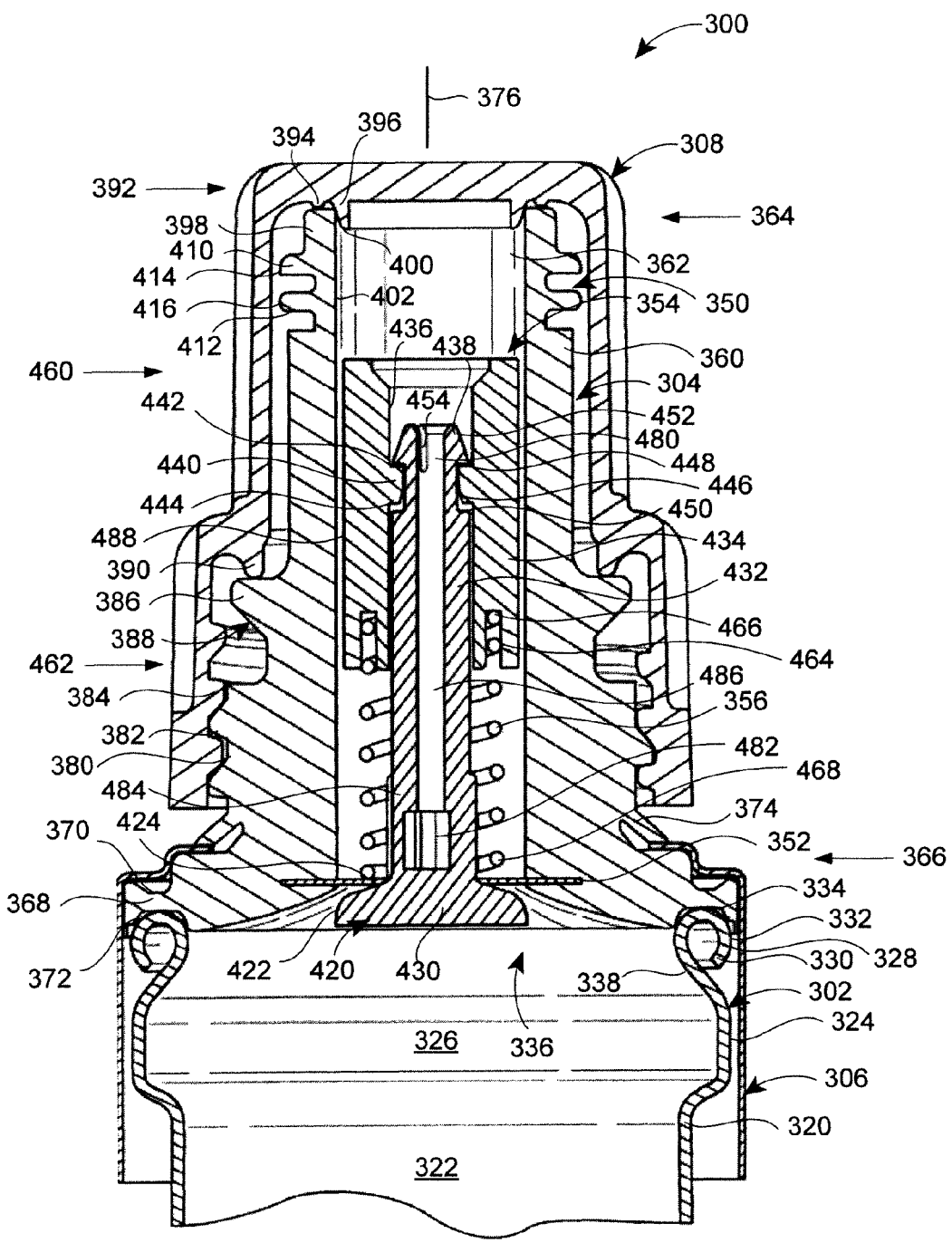
FIG. 4 is a fragmentary, cross-sectional view of another container according to the present disclosure, with a valve assembly in a closed position.
Figure 5:
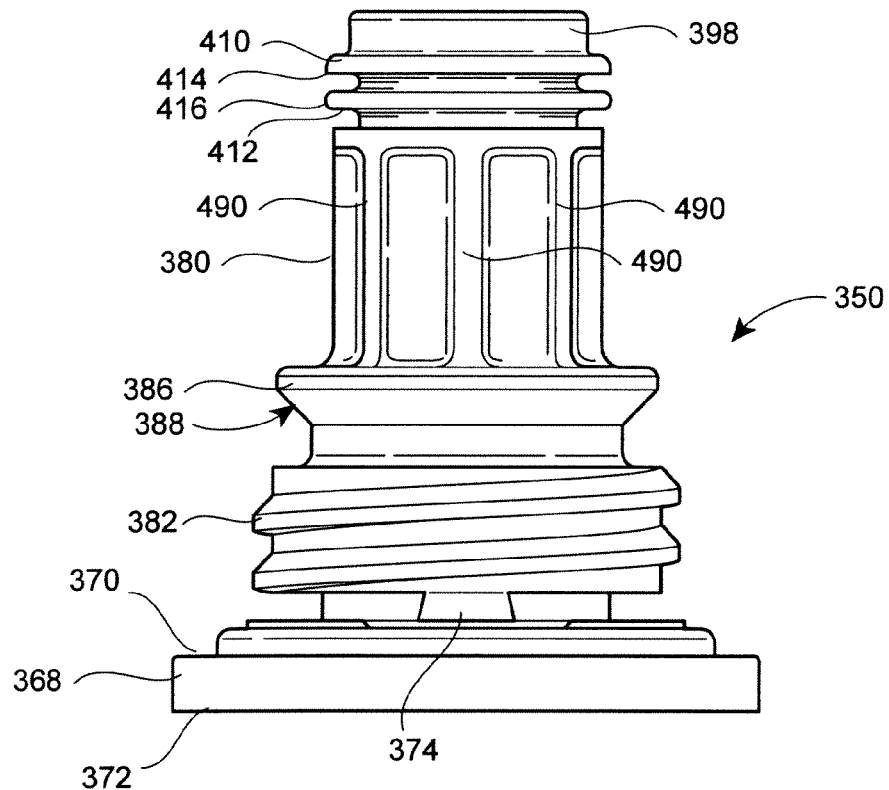
FIG. 5 is a side view of the conduit used in the container of FIG. 4.
Figure 6:
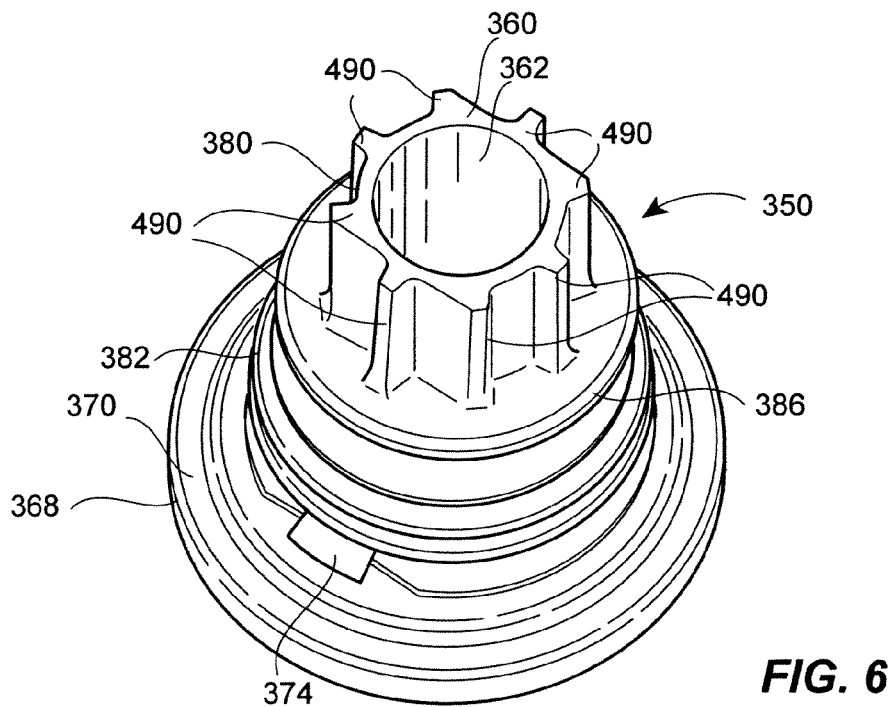
FIG. 6 is a perspective view, in partial cross-section, of the conduit used in the container of FIG. 4.

A further embodiment of a product according to the present disclosure is illustrated in FIGS. 4-6. The product may include a container 300, with a receptacle 302, a valve assembly 304, and a ferrule 306. The container 300 also may include a cap 308 that is fitted over the end of the valve assembly 304, as illustrated. The cap 308 may provide a barrier to anesthetic loss as well as limiting access to and contamination of the valve assembly 304.

The receptacle 302 (which may in the form of a bottle as illustrated) has a wall 320 that defines an interior space 322 and a neck 324 with a passage 326 in fluid communication with the interior space 322. An anesthetic may be disposed in the interior space 322, such as any one or all of the anesthetics referenced above relative to container 100, to define a pharmaceutical product. In addition, the receptacle 302 has a flange 328, preferably positioned at the neck 324 of the receptacle 302. As illustrated in FIG. 1, the flange 328 may be formed by rolling the wall 320 of the receptacle 302 about approximately 360 degrees, such that an edge 330 of the wall 320 almost abuts or abuts an exterior surface 332 of the wall 320 to define a rim 334 about an opening 336 in communication with the passage 326.

According to an embodiment of the present disclosure, the receptacle 302 is made of metal, for example, steel, aluminum or an aluminum alloy; according to still other embodiments, the receptacle 302 may be made of a polymer, such as polyethylene terephthalate (PET). Alternatively, the receptacle 302 may be made of glass. According further embodiments, a layer of a polymer or other material may define an exterior and/or interior surface 332, 338 of the wall 320.

The valve assembly 304 is attached to the receptacle 302 to control flow of fluids (e.g., anesthetic) in and out of the receptacle 302 through the passage 326. The valve assembly 304, as illustrated, includes a conduit 350 with an annular plate 352 embedded (e.g., molded) therein, a valve member (or core) 354, and a resilient or biasing member 356. As was the case with the valve assembly 104, the conduit 350 (except for the plate 352) and the valve member 354 may be made of low-density polyethylene. Other elements may be included as well, but as was the case with valve assembly of the container 100, the valve assembly 304 is designed to be gasketless in regard to the interface between the valve assembly 304 and the receptacle 302, and the interface within the valve assembly 304 between the valve member 354 and the conduit plate 352.

Beginning then with the conduit 350, the conduit 350 has a generally cylindrical wall 360 that defines a cylindrical conduit passage 362 with a first end 364 and a second end 366. The conduit 350 may also have a conduit flange 368 that depends outwardly from the wall 360. The conduit flange 368 is disposed proximate to the second end 366 of the passage 362, as illustrated. The conduit flange 368 has opposing first and second surfaces 370, 372.

Although no gasket is disposed between conduit 350 and the receptacle 302, a fluid-tight seal is formed. In particular, a layer of resilient polymer may define the exterior surface 332 of the receptacle 302, at least in the region of the neck 324 of the receptacle 302. For example, a layer of low-density polyethylene may be disposed on a layer of aluminum or aluminum alloy in the region of the neck 324 of the receptacle 302 to define the wall 320. According to certain embodiments, the low-density polyethylene may be applied using powder coating techniques, in particular where the wall 320 of the receptacle 302 is includes a layer of aluminum or an aluminum alloy. Other methods of including or applying the low-density polyethylene may also be used. As noted above, the entirety of the wall 320 of the receptacle 302 need not include the layer of low-density polyethylene, and the discussion above as to the aspects of the wall of the container 100 in this regard applies equally here.

In addition, the conduit flange 368 may be formed to complement the rim 334 of the receptacle 302 to assist in the formation of a fluid-tight seal between the receptacle 302 and the valve assembly 304, and in particular the conduit 350. To this end, the surface 372 of the conduit flange 368 may have a concave arcuate or semi-arcuate shape with a curvature similar to that of the convex arcuate shape of the rim 334 of the receptacle 302. The mating nature of the rim 334 and the surface 372 may also assist in seating the valve assembly 304 (and in particular the conduit 350) onto the receptacle 302.

As illustrated, the ferrule 306 is disposed over at least a portion of the conduit flange 368 and about at least a portion of the neck 324 to attach the valve assembly 304 to the receptacle 302, as discussed relative to the container 100 above. Moreover, as seen in cross-section in FIG. 4 and as a side view in FIG. 5, the conduit 350 includes a pair of angled tabs 374 that depend from the wall 360 of the conduit 350. These tabs 374 have a thickness that permits their deflection radially inward in the direction of a longitudinal axis 376 of the conduit 350 to permit the ferrule 306 to pass by the tabs 374 as the ferrule 306 is fitted over the conduit 350. On the other hand, the tabs 374 will deflect radially outwardly to resist removal of the ferrule 306 if an attempt is made to remove the ferrule 306 from the conduit 350 once the ferrule 306 is in place. The tabs 374 thus provide a mechanism to secure the ferrule 306 to the conduit 350 prior to crimping the ferrule 306 about the neck 324 to attach the valve assembly 304 to the receptacle 302.

As noted above, other methods of attachment between the valve assembly 304 and the receptacle 302 may be used. As such, the valve assembly 304 may be considered separately from the receptacle 302 in the form of an adapter.

Moving along an exterior surface 380 of the conduit 350, it will be recognized that the conduit 350 has a threaded section 382 that mates with a threaded section 384 of the cap 308. The mating threaded sections 382, 384 of the conduit 350 and cap 308 releasably secure the cap 308 to the conduit 350. To some extent, the mating sections 382, 384 may also work to seal the valve assembly 304 to limit the escape of anesthetic from the receptacle 302, or to limit infiltration of contaminants into the receptacle 302. However, there are other features provided on the cap 308 that also assist in limiting the escape of anesthetic from the receptacle.

For example, the conduit 350 also features a flared flange 386 that may be used to releasably secure the conduit 350 (and associated container 300) to a vaporizer while the conduit 350 is fitted into a vaporizer port of the vaporizer. For example, a latching mechanism may abut against the sloped region 388 of the flange 386 to limit or prevent the axial movement of the container 300 out of a vaporizer port. See U.S. Pat. No. 5,617,906. As illustrated in FIG. 4, the cap 308 includes an annular wall or ring 390 that depends axially from the cap 308 to the flange 386, and abuts the flange 386 to limit or prevent escape of anesthetic from (or infiltration of contaminant into) the receptacle 302.

Further, the cap 308 may have a closed end 392 with a pair of concentric annular walls, or rings, 394, 396. The first annular wall 394 may be disposed a greater distance radially from the longitudinal axis 376 than the second annular wall 396. The first annular wall 394 abuts an open end 398 of the conduit 350 to define a first sealing relationship with the open end 398 of the conduit 350. On the other hand, the second annular wall 396 has a sloped surface 400 that abuts an inner surface 402 of the conduit 350 that defines the passage 362 to define a second sealing relationship with the open end 398 of the conduit 350.

While the illustrated embodiment thus has several structures on the cap 308 and the conduit 350 that cooperate to limit the escape of anesthetic from the receptacle 302 (threaded sections 382, 384; flange 386, wall 390; end 398, wall 394; surface 402, wall 396), it is not necessary for a single embodiment to include each of these structures. Instead, an embodiment according to the present disclosure may include one or more of the structures, or none of the structures. However, it is believed that by including one or more of these cooperating structures between the cap 308 and the conduit 350, the gasket that is conventionally used to provide a fluid-tight seal between the cap 308 and the conduit 350 (see FIG. 1) may be omitted.

Returning to the open end 398 of the conduit 350, it will be recognized that the conduit 350 also includes a pair of annular rings 410, 412 that depend radially outward (relative to the axis 376) from the exterior surface 380 of the conduit 350. The rings 410, 412 are formed integrally (i.e., as a single piece) with the conduit 350, and are spaced from each other along the axis 376. The rings 410, 412 may replace the o-ring structure used in conventional valve assemblies. See, for example, U.S. Pat. No. 5,617,906.

In this regard, both rings 410, 412 may seal with the inner surface of a vaporizer port to limit the passage of anesthetic between the conduit 350 and the vaporizer port. In fact, the mold that is used to form the conduit 350 may be a three-piece mold, with one parting plane disposed along the circumferential edge 414 of the ring 410. The separation of the mold along this plane gives the ring 410 its sharp edge 414 and asymmetric profile in cross-section; however, the ring 410 has no axial parting plane that might interrupt the seal between the ring 410 (particularly, the edge 414) and the inner surface of the vaporizer port. By comparison, the ring 412 has a symmetrical profile with a rounded edge 416, but may have one or more ridges formed on the edge 416 by the axial parting planes of the remainder of the mold. However, it is believed that the arrangement of rings 410, 412 provides a suitable seal in operation.

In addition to sealing, the rings 410, 412 may serve other roles as well. For example, the ring 410 may provide a centering function when introducing the conduit 350 into a vaporizer port. Further, the ring 410 may limit impacts with the ring 412 that would otherwise damage the ring 412, potentially affecting the ability of the ring 412 to cooperate with an inner surface of the vaporizer port.

Returning now to the passage 362, the valve member 354 is disposed in the passage 362 to control the passage of anesthetic through the passage 362. The valve member 354 has a first end 420 that is disposed in the second end 366 of the passage 362 when the valve member 354 is in the closed position (as seen in FIG. 4). The valve member 354 is spaced from the second end 366 of the passage 362 when the valve member 354 is in the open position (similar to FIG. 3).

The valve member 354 may have conical or tapered surface 422 formed at the first end 420. While the surface 422 has a curved profile as illustrated, it will be recognized that the surface 422 may actually have a sloped profile instead, for example. According to the illustrated embodiment, the rim 424 of the annular conduit plate 352 may directly contact the surface 422 with the valve member 354 in the closed position. The rim 424 is configured to concentrate the contact forces between the plate 352 and surface 422 to define a fluid-tight seal. Accordingly, the second end 366 of the conduit passage 362 and the valve member 354 may have a gasketless, fluid-tight seal formed therebetween with the valve member 354 in the closed position (FIG. 1). It will be recognized that other configurations that define gasketless, fluid seals may be used as well.

Figure 2:
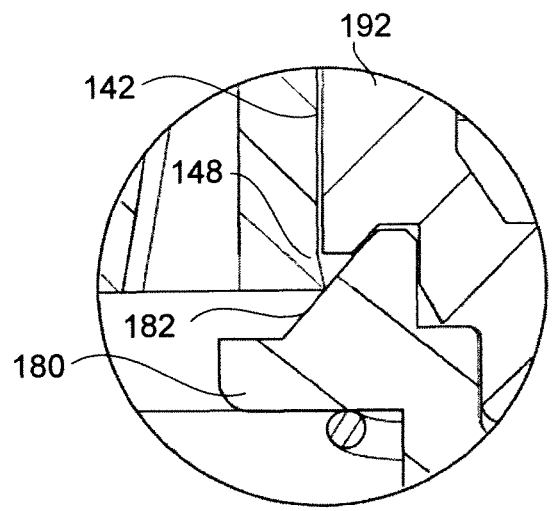
FIG. 2 is an enlarged, partial cross-sectional view of a container according to the present disclosure, highlighting the sharp-edged rim of the conduit.

In this regard, the embodiment of FIGS. 4-6 shares certain similarities with the embodiment of FIGS. 1-3, while exhibiting certain differences. Both the embodiments of FIGS. 1-3 and FIGS. 4-6 may use a low-density polyethylene of a medical grade. Such grades typically limit the use of fillers, thereby providing a more pure grade that in turn limits leachables or extractables. According to one such embodiment, the medical grade low-density polyethylene may be manufactured and sold under the 20 Series DPE-2020T grade by E.I. du Pont de Nemours and Company, Inc.

Similar to the embodiment of FIGS. 1-3, the embodiment of FIGS. 4-6 relies on the abutment of the edge of a structure of the conduit 350 (in the case of the embodiment of FIG. 4-6, the plate 352 embedded in the conduit 350) and the valve member 354 to define a gasketless, fluid-tight seal. However, rather than rely upon the plastic conduit 350 to maintain a sharp edge that abuts and seals against the valve member, the conduit 350 features a metal annular plate 352 (such as a stainless steel plate) that provides the required rigidity at the rim 424 to provide the sealing relationship with the plastic valve member 354. Alternatively, the plate 352 may be formed using a plate with a wall defined with an inner layer of metal and a non-metallic outer layer, such as a polymer, like polyethylene, an epoxyphenolic resin, or other materials.

The presence of the plate 352 also permits a further redesign of the valve member 354 relative to the embodiment of FIGS. 1-3 as it relates to the biasing of the valve member 354. It will be recognized that the valve member 354 includes a plate (or core seat) 430 and a tube (or core extension) 432 formed integrally (i.e. as a single piece), as illustrated. It will be recognized that other valve members may be designed wherein the plate 430 and tube 432 may be formed as a separate units (i.e., not as a single piece). Thus, the illustrated embodiment is not intended to be limiting in this regard.

Unlike the valve member of the embodiment of FIGS. 1-3, the valve member 354 includes a collar 434 that is fitted about a portion of the tube 432. To this end, the collar 434 has a central passage 436 to receive a first end 438 of the tube 432. The collar 434 also has an inwardly depending flange or step 440 that cooperates with the first end 438 of the tube 432. The step 440 defines surfaces 442, 444 that face in opposite directions along the axis 376. The tube 432 has a notch or groove 446 formed at the first end to receive the step 440 therein, the groove having facing surfaces 448, 450 that face and may abut the surfaces 442, 444 of the step 440. The surfaces 448 may be defined on one of a plurality of projections or hooks 452 that depend through the passage 436 past the step 440. The hooks 452 are separated from each other by spaces 454 to permit the hooks 452 to flex radially inward when the first end 438 of the tube 432 is introduced into the collar 434 and then snap back into place once the hooks 452 are past the step 440.

The collar 434 also has first and second ends 460, 462, with the second end 462 having an annular notch or groove 464 formed therein. The groove 464 receives a first end 466 of the biasing member 356, with the second end 468 of the biasing member 356 abutting the annular plate 352. The force of the biasing member 356 thus urges the plate 430 into engagement with the rim 424 of the plate 352. Consequently, the valve assembly 304 does not include a cage, as illustrated in the embodiment of FIGS. 1-3.

As in the embodiment of FIGS. 1-3, the tube 432 is an exemplary structure or partition that may be included in the valve member 354 to guide the flow of more than one fluid at a time through the passage 362. In particular, the tube 432 has an opening 480 at the first end 438 and at least one opening 482 at a second end 484 with a passage 486 connecting the two ends 438, 484. While the tube 432 is illustrated as coaxial with the conduit 350, this need not be the case according to all embodiments of the present disclosure. The ends 438, 484 and the passage 486 provide a return path for gaseous anesthetic to flow into the receptacle 302 from the vaporizer.

On the other hand, the collar 434 is sized so that a surface 488 of the collar 434 and the facing surface 402 of the conduit 350 are spaced from each other to permit liquid anesthetic to flow therebetween. The collar 434 may include one or more ribs defining passages therebetween to permit liquid anesthetic to flow about the collar 434 more freely, as was the case with the embodiment of FIGS. 1-3 as discussed above. When the valve member 354 (and in particular the plate 430) is spaced from the plate 352, liquid anesthetic may flow between the valve member 354 and the plate 352, between the valve member 354 (in particular, the collar 434) and the conduit 350 and out of the open first end 364 of the conduit 350 into the vaporizer port.

Finally, in discussing the embodiment of FIGS. 4-6, one additional distinction should be noted relative to the embodiment of FIGS. 1-3. With reference to FIG. 6, it is noted that the conduit 350 has a generally cylindrical shape, but the exterior surface 380 of the conduit is not circular as viewed in plane perpendicular to the axis 376 of the conduit 350. Instead, the conduit 350 has a plurality of .ribs 490 that depend radially outwardly from the wall 360 of the conduit 350. While eight such ribs 490 are illustrated in FIG. 6, other embodiments may include a greater or lesser number of ribs 490. Furthermore, while the ribs 490 are relatively equally spaced about the periphery of the conduit 350, this need not be the case according to all embodiments of the present disclosure. The thickness of the wall 360 between the ribs 490 need not be uniform (i.e., of constant thickness); instead, as illustrated, the thickness of the wall 360 may vary so as to facilitate the separation of the mold used to form the conduit 350 along its parting plane.

It will be appreciated that the advantageous structures at the interface between the valve assembly and the receptacle and within the valve assembly disclosed above need not both be present in all containers according to the present disclosure. That is, the illustrated containers include gasketless interfaces between the valve assembly and the receptacle, and between the valve member and the conduit. Accordingly, the illustrated valve assembly is constructed so that at least the surface of any component of the assembly that will come into contact with the anesthetic on its storage or passage from the receptacle to the vaporizer is made of a metal or low-density polyethylene, and provides a fluid-tight seal to prevent the escape of the anesthetic without the use of a gasket in the closed configuration. However, in a particular embodiment according to the present disclosure, the gasketless interface between the valve assembly and the receptacle may be used with a conventional seal present at the interface between the valve member and the conduit. Similarly, the gasketless interface between the valve member and the conduit may be used with a gasket disposed between the valve assembly and the receptacle. Such a gasket may be formed of polyethylene so that the surfaces that come into contact with the anesthetic are made of a metal or polyethylene, in particular low-density polyethylene. The illustrated embodiment is not intended to limit the claims, but to illustrate the manifold advantages of a container including both gasketless interfaces and the particular material selections according to the present disclosure.

What is claimed is:
1. An anesthetic container comprising:
  a receptacle for holding the anesthetic and having a wall defining a interior space and a passage in fluid communication with the interior space; and
  a valve assembly that is attachable or is attached to the receptacle to control flow of anesthetic through the passage in the receptacle to a vaporizer, the valve assembly having a closed configuration when the flow of anesthetic from the receptacle is limited and an open configuration when the flow of anesthetic is enabled, wherein the valve assembly is constructed so that at least the surface of any component of the assembly that will come into contact with the anesthetic on its storage or passage from the receptacle to the vaporizer is made of a metal or low-density polyethylene and wherein the valve assembly provides a fluid-tight seal to prevent the escape of the anesthetic without the use of a gasket in the closed configuration; and wherein the valve assembly comprises:

a conduit comprising low-density polyethylene and having a wall defining a conduit passage with a first end and a second end; and a valve member comprising low-density polyethylene and having a first end that is disposed in the second end of the conduit passage when the valve assembly is in the closed configuration, and that is spaced from the second end of the conduit passage when the valve assembly is in the open configuration, the second end of the conduit passage and the valve member having a gasketless, fluid-tight seal therebetween with the valve assembly in the closed configuration.

2. The anesthetic container according to claim 1, wherein the conduit comprises a conduit flange depending outward from the wall, and the conduit flange is disposed in direct contact with the receptacle to define a gasketless, fluid-tight seal therebetween.

3. The anesthetic container according to claim 1, further comprising a cap, the cap having at least one annular wall that abuts the conduit with the cap releasably secured to the valve assembly to define a gasketless, fluid-tight seal therebetween.

4. The anesthetic container according to claim 1, further comprising a halogenated inhalation anesthetic contained within receptacle, the anesthetic selected from the group of halogenated anesthetics consisting of sevoflurane, desflurane, isoflurane, enflurane, methoxyflurane and halothane.

5. The anesthetic container according to claim 1, wherein the conduit includes a rim disposed about the second end of the conduit passage, and the valve member includes a tapered surface formed at the first end, the rim directly contacting the tapered surface with the valve assembly in the closed configuration to define a fluid-tight seal.

6. The anesthetic container according to claim 5, wherein the conduit wall forms the rim, and the rim is formed with an edge that concentrates contact forces between the rim and the tapered surface.

7. The anesthetic container according to claim 6, wherein the edge is formed as a sharp edge.

8. The anesthetic container according to claim 5, wherein the conduit includes an annular conduit plate embedded in the conduit at the second end, the annular plate defining the rim.

9. The anesthetic container according to claim 8, wherein the valve member comprises a plate at the first end of the valve member, a tube that passes through the annular conduit plate, and a collar that is attached to the tube at the second end of the valve member, and a biasing member disposed between the annular conduit plate and the collar.

10. The anesthetic container according to claim 1, wherein the conduit comprises a conduit flange depending outward from the wall, and the valve assembly comprises a cage having a cage flange that is disposed between the conduit flange and the receptacle and that is in direct contact with the receptacle to define a gasketless, fluid-tight seal therebetween.

11. The anesthetic container according to claim 10, further comprising a biasing member disposed between the valve member and the cage.

12. The anesthetic container according to claim 1, wherein the wall of the receptacle comprises a layer of low-density polyethylene with the valve assembly abutting at least in part the layer of low-density polyethylene.

13. The anesthetic container according to claim 12, wherein the wall of the receptacle has an exterior surface and the layer of low-density polyethylene defines at least in part the exterior surface of the wall.

14. The anesthetic container according to claim 13, wherein the low-density polyethylene is powder coated onto a layer of aluminum or aluminum alloy.

* * * * *